United States Patent
Qiu et al.

(10) Patent No.: US 12,134,087 B2
(45) Date of Patent: Nov. 5, 2024

(54) METHOD FOR PREPARING PICKERING MINIEMULSION AND ITS CATALYTIC APPLICATION

(71) Applicant: Dalian University of Technology, Dalian (CN)

(72) Inventors: Jieshan Qiu, Dalian (CN); Chang Yu, Dalian (CN); Lin Ni, Dalian (CN); Ji Wen, Jiangyou (CN)

(73) Assignee: Dalian University of Technology, Dalian (CN)

( * ) Notice: Subject to any disclaimer, the term of this patent is extended or adjusted under 35 U.S.C. 154(b) by 0 days.

(21) Appl. No.: 18/479,002

(22) Filed: Sep. 30, 2023

(65) Prior Publication Data

US 2024/0116040 A1     Apr. 11, 2024

(30) Foreign Application Priority Data

Oct. 5, 2022   (CN) .......................... 202211218392.X

(51) Int. Cl.
| | |
|---|---|
| *B01J 35/23* | (2024.01) |
| *B01J 21/18* | (2006.01) |
| *B01J 23/46* | (2006.01) |
| *B01J 37/00* | (2006.01) |
| *B01J 37/02* | (2006.01) |
| *B01J 37/04* | (2006.01) |
| *B01J 37/16* | (2006.01) |
| *B01J 37/34* | (2006.01) |
| *C07C 45/29* | (2006.01) |

(52) U.S. Cl.
CPC .............. *B01J 35/23* (2024.01); *B01J 21/18* (2013.01); *B01J 23/462* (2013.01); *B01J 37/009* (2013.01); *B01J 37/0221* (2013.01); *B01J 37/04* (2013.01); *B01J 37/16* (2013.01); *B01J 37/343* (2013.01); *C07C 45/294* (2013.01)

(58) Field of Classification Search
CPC . B01J 35/23; B01J 21/18; B01J 23/462; B01J 37/009; B01J 37/04; B01J 37/16; C07C 45/294
See application file for complete search history.

(56) References Cited

U.S. PATENT DOCUMENTS

2022/0380217 A1* 12/2022 Katsurao ................ C09K 11/65

OTHER PUBLICATIONS

Zhou et al. Carbon quantum dots-stabilized Pickering emulsion to prepare NIR light-responsive PLGA drug delivery system. Materials Today Communications, vol. 23, 1-5. (Year: 2020).*
Zhai et al. Inverse Pickering emulsions stabilized by carbon quantum dots: Influencing factors and their application as templates. Chemical Engineering Journal, vol. 345, 209-220. (Year: 2018).*
CNIPA, Notification of a First Office Action for CN202211218392. X, Jun. 22, 2023.
Dalian University of Technology (Applicant), Replacement claims (allowed) of CN202211218392.X, Jul. 24, 2023.
CNIPA, Notification to grant patent right for invention in CN202211218392.X, Jul. 27, 2023.

* cited by examiner

*Primary Examiner* — Sikarl A Witherspoon
(74) *Attorney, Agent, or Firm* — Hemisphere Law, PLLC; Zhigang Ma

(57) ABSTRACT

A submicron-sized Pickering miniemulsion system stabilized by carbon quantum dots solid nanoparticles for biphasic catalysis is disclosed, which breaks the existing limits for homogenization of the immiscible biphasic system and overcomes the issues for big size of solid particles-stabilized emulsion droplets. A method for producing the carbon quantum dot-based catalysts and a process of establishing the Pickering miniemulsion system for biphasic reaction with enhanced catalytic efficiency are also disclosed. The carbon quantum dot-stabilized Pickering miniemulsion features a pH-responsive behavior, with a reversible transition between the emulsification and demulsification, triggering the easy & facile product separation and emulsifier/catalyst recycling in one reaction vessel.

8 Claims, 1 Drawing Sheet

METHOD FOR PREPARING PICKERING MINIEMULSION AND ITS CATALYTIC APPLICATION

TECHNICAL FIELD

The disclosure relates to the field of emulsion catalysis technologies, and more particularly to a construction method and an application of a Pickering miniemulsion catalysis system.

BACKGROUND

Compared with a traditional single-phase organic system, an organic solvent-water biphasic reaction system can solubilize water-soluble substrates, so it is widely used as a green reaction system in various reactions, such as oxidation, epoxidation, hydrogenation, Suzuki coupling and hydroformylation, etc. Reaction characteristics of the organic solvent-water biphasic reaction system are that reaction substrates are dissolved in different liquid phases, and the reaction occurs at an interface of two phases. At the same time, in some special substrates, using a difference in solubility between reactants and a product in different liquid phases, the product can be separated through simple phase separation. However, in an immiscible biphasic system, a limited reaction boundary area makes it difficult to contact between the reaction substrates/reaction substrates and the catalyst, which is not conducive to a progress of catalytic reaction. Generally, the efficiency of biphasic catalytic reaction (i.e., biphasic catalytic reaction) can be improved by adding co-solvents, surfactants, etc., but the addition of additional additives will bring new difficulties to the separation and purification of products.

The Pickering emulsion catalysis technology that has emerged since this century uses solid particles to directly emulsify the biphasic system to form kinetically stable Pickering emulsion, which can increase the biphasic boundary area without other additives, overcome the diffusion limitation of substrates, and increase the catalytic rate. Solid emulsifiers can be directly used as catalysts. So far, researchers have discovered and designed a variety of solid particles that can be used as Pickering emulsion catalysts, such as surface-modified silicon dioxide, titanium dioxide, titanium silicate, polymer, carbon nanotubes, graphene oxide and their composites, etc. However, a size of the Pickering emulsion is usually in a micron range, and a droplet size is in a range of 10 micrometres ($\mu m$) to 1000 $\mu m$, which can only create a reaction boundary area of $10^3$-$10^5$ $m^2 \cdot m^{-3}$. Therefore, it is urgent to further reduce the droplet size to promote mass transfer and improve catalytic efficiency. The droplet size of the Pickering miniemulsion is in a submicron range (i.e., 0.1-1 $\mu m$), and a reaction boundary area provided by the Pickering emulsion can be increased by 2-3 orders of magnitude to $10^6$-$10^7$ $m^2 \cdot m^{-3}$, which will greatly increase the reaction rate of the biphasic catalytic reaction, so it is necessary to develop recyclable solid catalysts to stabilize miniemulsions and construct Pickering miniemulsion catalytic systems.

SUMMARY

In order to solve the above problems, the disclosure aims to provide a method for constructing a Pickering miniemulsion catalytic system, and an application of the Pickering miniemulsion catalytic system in a biphasic catalytic reaction. At the same time, the Pickering miniemulsion catalytic system is stimuli-responsive, which can break the emulsion and induce phase separation under external stimuli such as pH, thereby realizing the recovery and in-situ recycling of catalysts.

In order to realize the above-mentioned purpose of the disclosure and solve the problems existing in the prior art, the technical schemes of the disclosure are as follows.

A method for constructing a Pickering miniemulsion catalytic system includes the following steps 1 and 2.

In step 1, preparing a Pickering miniemulsion catalyst/emulsifier, specifically includes the following step 1.1 and step 1.2.

In step 1.1, preparation of surface-modified carbon quantum dots:

firstly, carbon dots are modified by using an amine compound as a modifier and citric acid as a carbon source; the citric acid and the amine compound are added to absolute ethanol and stirred for 0.5 to 5 hours (h) until they are mixed evenly to obtain a mixture; a precipitate of the mixture is filtered and washed with ethanol several times; the amine compound is one selected from the group consisting of dodecylamine, tetradecylamine, hexadecylamine, and octadecylamine, and 1.5-3 grams (g) of the citric acid and 0.1-4 g of the amine compound are added into every 25 milliliters (mL) of the absolute ethanol; the obtained solid powder is dried at 50-90 degree Celsius (° C.), and then the dried powder is heated at 180-220° C. in air atmosphere for 0.5-2 h until the white powder is completely liquefied into orange liquid;

then, the orange liquid is dispersed into sodium hydroxide (NaOH) aqueous solution dropwise, and stirred at 35-50° C. for 24-48 h to obtain a dispersion; and a concentration of NaOH is 0.25 moles per liter (M) and a volume ratio of the NaOH aqueous solution to the orange liquid is 20:1;

finally, the dispersion is centrifuged in a high-speed centrifuge for 5-10 min at a rotating speed of 6000-9000 revolutions per minute (rpm) to obtain a supernatant, the supernatant is treated with a 500 Dalton (DA) dialysis membrane for 24-48 h to remove small molecular impurities and obtain yellow carbon dots solution; the yellow carbon dots solution is placed in an environment below −10° C. until the yellow carbon dots solution is completely frozen, and then dried in a freeze dryer for 2-5 days to obtain carbon dots solid powder (i.e., the surface-modified carbon quantum dots) with a size of 8-12 nanometers (nm).

In step 1.2, preparation of an emulsion catalyst:

the carbon dots solid powder and a metal salt are added into a mixed solution of water and ethanol and then stirred for 3-6 h to obtain a system; the metal salt is one selected from the group consisting of ruthenium chloride, palladium chloride and chloroplatinic acid; 20-1000 milligrams (mg) of the carbon dots solid powder and 1-50 mg of the metal salt are correspondingly added into every 50 mL of the mixed solution of water and ethanol, and a volume ratio of the water to the ethanol in the mixed solution of water and ethanol is 1:4; and after standing the system for 6-18 h, sodium borohydride ($NaBH_4$) aqueous solution is added dropwise into the system to perform reduction for 0.5-2 h until the system becomes a black suspension, and then the black suspension is centrifuged in a high-speed centrifuge for 15-35 min at a rotating speed of 18000-26000 rpm to obtain a solid emulsion catalyst (i.e., the emulsion catalyst); and 10 mL of the NaBH$_4$ aqueous solution with a concentration of 2 mg·mL$^{-1}$ is correspondingly added to every 50 mL of the mixed solution of water and ethanol.

In step 2, constructing the Pickering miniemulsion catalytic system, specifically includes the following steps 2.1 and 2.2.

In step 2.1, the obtained solid emulsion catalyst is dispersed in water to prepare a dispersion A with a concentration of 0.05-5 percentages by weight (wt %).

In step 2.2, the dispersion A is added to a vial with a water-immiscible organic solvent to obtain a mixture; a volume ratio of the dispersion A to the organic solvent is 2:1; the mixture in the vial is ultrasonically treated for 0.5-2 min, and then stirred for 10-20 min to emulsify the mixture and form a Pickering miniemulsion, and a droplet size of the Pickering miniemulsion is in a range of 0.1-1 μm; and the organic solvent is toluene, cyclohexane, dichloromethane, ethyl acetate, decalin or another water-insoluble organic substance.

An application of the Pickering miniemulsion catalytic system, includes: applying the Pickering miniemulsion catalytic system in a biphasic catalytic reaction, specifically including: adding a reactant and a water-soluble oxidant/reductant into the Pickering miniemulsion catalytic system, then uniformly stirring in an oil bath pot at 30-90° C. and reacting for 0.5-5 h; where a molar ratio of the reactant to the water-soluble oxidant/reductant is 1:3, and 2-10 millimoles (mmol) of the reactant are added into every 10 mL of the Pickering miniemulsion catalytic system; after the reacting, adding 1 M inorganic acid solution dropwise into the Pickering miniemulsion catalytic system until demulsification, thus realizing oil-water stratification; where a product is dissolved in an organic phase and a catalyst is dispersed in a water phase; the product in the organic phase is detected by gas chromatography to obtain its yield; and the water phase containing the catalyst is used as the dispersion A for repeated use in step 2.2; after adding several drops of NaOH solution (1 M) to tune the pH value to 10-11, the Pickering miniemulsion is regenerated by stirring; and the reactant includes alcohol, olefin or a nitro compound; and the oxidant is hydrogen peroxide (H$_2$O$_2$), the reductant is NaBH$_4$, and the inorganic acid includes hydrochloric acid solution, sulfuric acid solution, nitric acid and another inorganic acid.

Compared with the prior art, the disclosure has the following beneficial effects:
(1) The Pickering miniemulsion catalytic system constructed by the disclosure has a droplet size of 0.1-1 μm, which is much smaller than that of the Pickering emulsion catalytic system (a droplet size is 10-1000 μm), which can significantly increase the reaction boundary area and promote mass transfer.
(2) The Pickering miniemulsion catalytic system constructed by the disclosure can be used in an emulsion catalytic oxidation process of an alcohol organic compound in the presence of H$_2$O$_2$ and an emulsion catalytic reduction process of an unsaturated hydrocarbon and a nitro compound in the presence of NaBH$_4$. At the same temperature, compared with the traditional Pickering emulsion catalytic system, an emulsion catalytic oxidation reaction rate can be increased by 5-20 times and an emulsion catalytic reduction reaction rate can be increased by 8-15 times in the Pickering miniemulsion system constructed by the disclosure.
(3) The Pickering miniemulsion catalytic system constructed by the disclosure has pH-responsive characteristics, and emulsion demulsification and in-situ recycling of catalysts can be realized by changing the pH value of the solution.

DETAILED DESCRIPTION OF EMBODIMENTS

In view of many defects in the prior art, the inventor of the disclosure has put forward the technical schemes through long-term research and a lot of practice, and will further explain the technical schemes, their implementation processes and principles as follows. However, it should be understood that within the scope of the disclosure, the above technical features of the disclosure and the technical features described in detail in the following (embodiments) can be combined with each other to form a new or preferred technical scheme. The disclosure will be further explained with the embodiments. The materials and reagents used in the following embodiments can be obtained from commercial sources unless otherwise specified.

Embodiment 1

Figure 1:
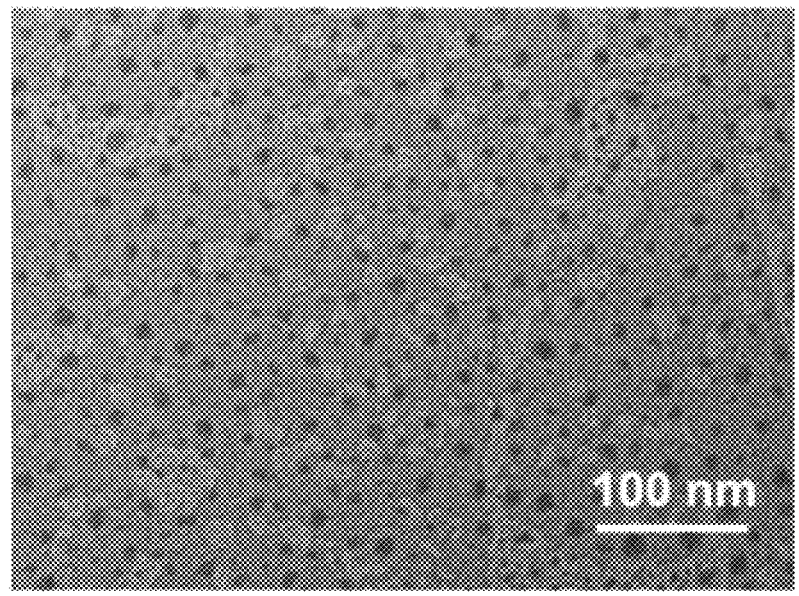
FIG. 1 illustrates a transmission electron microscope diagram of carbon dots prepared in Embodiment 1.

The 1.5 g of citric acid and 0.1 g of dodecylamine are added into 25 mL of absolute ethanol to obtain a mixture, and the mixture is stirred for 0.5 h until the mixture is uniform. A precipitate of the mixture is filtered and washed several times with ethanol to obtain solid powder. The obtained solid powder is dried at 50° C. to obtain the dried powder (i.e., white powder), and then the dried powder is heated at 180° C. in air atmosphere for 0.5 h until the white powder is completely liquefied into orange liquid. Then, the 1 mL of orange liquid obtained above is dispersed dropwise into 20 mL of NaOH aqueous solution, and a concentration of NaOH is 0.25 M. And the NaOH aqueous solution added with the orange liquid is stirred at 35° C. for 24 h to obtain a dispersion. Finally, the obtained dispersion is centrifuged in a high-speed centrifuge for 5 min at a rotation speed of 6000 rpm to obtain a centrifuged supernatant. The centrifuged supernatant is treated with a 500 DA dialysis membrane for 24 h to remove small molecular impurities and obtain yellow carbon dots solution. The obtained yellow carbon dots solution is placed in an environment of −10° C. until it is completely frozen and then dried in a freeze dryer for 2 days to obtain carbon dots solid powder with an average size of 10 nm, as shown in FIG. 1.

The 1000 mg of carbon dots (i.e., the obtained carbon dots solid powder) and 50 mg of ruthenium chloride are added into a mixed solution of 10 mL of water and 40 mL of ethanol to obtain a system, and then the system is stirred for 6 h, followed by standing the system for 18 h. After standing the system for 18 h, 10 mL of NaBH$_4$ aqueous solution with a concentration of 2 mg·mL$^{-1}$ is dropped into the above system to perform reduction for 2 h until the solution becomes a black suspension, and then the black suspension is centrifuged in a high-speed centrifuge for 35 min at a speed of 26000 rpm to obtain a solid emulsion catalyst.

Figure 2:
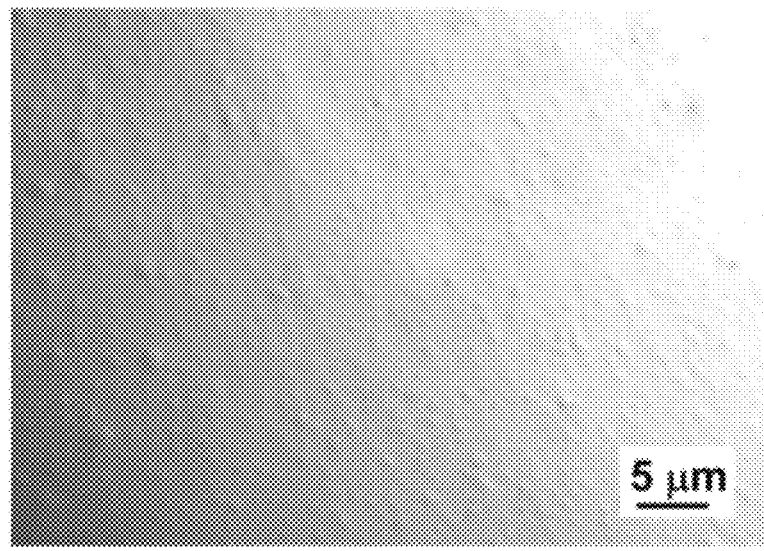
FIG. 2 illustrates an optical microscope diagram of a Pickering miniemulsion prepared in Embodiment 1.

The obtained solid emulsion catalyst is dispersed in water to prepare a dispersion with a concentration of 0.05 wt %. The 12 mL of dispersion and 6 mL of toluene are added into a vial to perform ultrasonic treatment for 0.5 min to obtain a mixture, and then the mixture is stirred for 10 min to emulsify the above mixture and form a Pickering miniemulsion, with a droplet size in a range of 0.1-1 µm, as shown in FIG. 2. The 2 mmol of benzyl alcohol and 6 mmol of $H_2O_2$ are added into the catalytic system formed by the 10 mL of Pickering miniemulsion, and stirred evenly in an oil bath pot at 90° C. and reacted for 0.5 h. After the reaction, several drops of 1 M of hydrochloric acid solution are added into the system until demulsification, thus realizing oil-water stratification. A product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. Benzaldehyde as the product in the organic phase can be detected by gas chromatography with a yield of 99.9%. The water phase containing the catalyst can be used as the dispersion A to repeat the reaction step for recycling, and the catalyst activity is not attenuated after 10 times of recycling reaction.

Embodiment 2

The 3 g of citric acid and 4 g of tetradecylamine are added into 25 mL of absolute ethanol to obtain a mixture, and the mixture is stirred for 5 h until the mixture is uniform. A precipitate of the mixture is filtered and washed several times with ethanol to obtain solid powder. The obtained solid powder is dried at 90° C. to obtain the dried powder (i.e., white powder), and then the dried powder is heated at 220° C. in air atmosphere for 2 h until the white powder is completely liquefied into orange liquid. Then, the 2 mL of orange liquid obtained above is dispersed dropwise into 40 mL of NaOH aqueous solution, and a concentration of NaOH is 0.25 M. And the NaOH aqueous solution added with the orange liquid is stirred at 50° C. for 48 h to obtain a dispersion. Finally, the obtained dispersion is centrifuged in a high-speed centrifuge for 10 min at a rotation speed of 9000 rpm to obtain the centrifuged supernatant. The centrifuged supernatant is treated with a 500 DA dialysis membrane for 48 h to remove small molecular impurities and obtain yellow carbon dots solution. The obtained yellow carbon dots solution is placed in an environment of −30° C. until it is completely frozen and then dried in a freeze dryer for 5 days to obtain carbon dots solid powder with an average size of 12 nm.

The 20 mg of carbon dots (i.e., the obtained carbon dots solid powder) and 1 mg of palladium chloride are added into a mixed solution of 10 mL of water and 40 mL of ethanol to obtain a system, and then the system is stirred for 3 h, followed by standing the system for 6 h. After standing the system for 6 h, 10 mL of $NaBH_4$ aqueous solution with a concentration of 2 $mg \cdot mL^{-1}$ is dropped into the above system to perform reduction for 0.5 h until the solution becomes a black suspension, and then the black suspension is centrifuged in a high-speed centrifuge for 15 min at a speed of 18000 rpm to obtain a solid emulsion catalyst.

The obtained solid emulsion catalyst is dispersed in water to prepare a dispersion A with a concentration of 5 wt %. The 10 mL of dispersion A and 5 mL of hexamethylene are added into a vial to perform ultrasonic treatment for 2 min to obtain a mixture, and then the mixture is stirred for 20 min to emulsify the above mixture and form a Pickering miniemulsion, with a droplet size in a range of 0.1-1 µm. The 10 mmol of styrene and 30 mmol of $NaBH_4$ are added into the catalytic system formed by the 10 mL of Pickering miniemulsion, and stirred evenly in an oil bath pot at 30° C. and reacted for 0.5 h. After the reaction, several drops of 1 M of sulfuric acid solution are added into the system until demulsification, thus realizing oil-water stratification. Ethylbenzene as a product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. The ethylbenzene in the organic phase can be detected by gas chromatography with a yield of 100%. The water phase containing the catalyst can be used as the dispersion A to repeat the reaction step for recycling, and the catalyst activity is not attenuated after 4 times of recycling reaction.

Embodiment 3

The 2 g of citric acid and 2 g of hexadecylamine are added into 25 mL of absolute ethanol to obtain a mixture, and the mixture is stirred for 3 h until the mixture is uniform. A precipitate of the mixture is filtered and washed several times with ethanol to obtain solid powder. The obtained solid powder is dried at 70° C. to obtain the dried powder (i.e., white powder), and then the dried powder is heated at 200° C. in air atmosphere for 1 h until the white powder is completely liquefied into orange liquid. Then, the 1 mL of orange liquid obtained above is dispersed dropwise into 20 mL of NaOH aqueous solution, and a concentration of NaOH is 0.25 M. And the NaOH aqueous solution added with the orange liquid is stirred at 40° C. for 36 h to obtain a dispersion. Finally, the obtained dispersion is centrifuged in a high-speed centrifuge for 8 min at a rotation speed of 8000 rpm to obtain a centrifuged supernatant. The centrifuged supernatant is treated with a 500 DA dialysis membrane for 36 h to remove small molecular impurities and obtain yellow carbon dots solution. The obtained yellow carbon dots solution is placed in an environment of −20° C. until it is completely frozen and then dried in a freeze dryer for 4 days to obtain carbon dots solid powder with an average size of 8 nm.

The 500 mg of carbon dots (i.e., the obtained carbon dots solid powder) and 25 mg of chloroplatinic acid are added into a mixed solution of 10 mL of water and 40 mL of ethanol to obtain a system, and then the system is stirred for 5 h, followed by standing the system for 12 h. After standing the system for 12 h, 10 mL of $NaBH_4$ aqueous solution with a concentration of 2 $mg \cdot mL^{-1}$ is dropped into the above system to perform reduction for 1 h until the solution becomes a black suspension, and then the black suspension is centrifuged in a high-speed centrifuge for 20 min at a speed of 20000 rpm to obtain a solid emulsion catalyst.

The obtained solid emulsion catalyst is dispersed in water to prepare a dispersion A with a concentration of 2 wt %. The 6 mL of dispersion A and 3 mL of dichloromethane are added into a vial to perform ultrasonic treatment for 1 min to obtain a mixture, and then the mixture is stirred for 15 min to emulsify the above mixture and form a Pickering miniemulsion, with a droplet size in a range of 0.1-1 µm. The 5 mmol of nitrobenzol and 15 mmol of $NaBH_4$ are added into the catalytic system formed by the 10 mL of Pickering miniemulsion, and stirred evenly in an oil bath pot at 60° C. and reacted for 1 h. After the reaction, several drops of 1 M of nitric acid solution are added into the system until demulsification, thus realizing oil-water stratification. Aniline as a product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. The aniline in the organic phase can be detected by gas chromatography with a yield of 98.3%. The water phase containing the catalyst can be used as the dispersion A to repeat the reaction step for recycling, and the catalyst activity is not attenuated after 5 times of recycling reaction.

Embodiment 4

The 2 g of citric acid and 1.8 g of octadecylamine are added into 25 mL of absolute ethanol to obtain a mixture, and the mixture is stirred for 2 h until the mixture is uniform. A precipitate of the mixture is filtered and washed several times with ethanol to obtain solid powder. The obtained solid powder is dried at 80° C. to obtain the dried powder (i.e., white powder), and then the dried powder is heated at 200° C. in air atmosphere for 1.5 h until the white powder is completely liquefied into orange liquid. Then, the 1.5 mL of orange liquid obtained above is dispersed dropwise into 30 mL of NaOH aqueous solution, and a concentration of NaOH is 0.25 M. And the NaOH aqueous solution added with the orange liquid is stirred at 45° C. for 36 h to obtain a dispersion. Finally, the obtained dispersion is centrifuged in a high-speed centrifuge for 8 min at a rotation speed of 9000 rpm to obtain a centrifuged supernatant. The centrifuged supernatant is treated with a 500 DA dialysis membrane for 48 h to remove small molecular impurities and obtain yellow carbon dots solution. The obtained yellow carbon dots solution is placed in an environment of −20° C. until it is completely frozen and then dried in a freeze dryer for 5 days to obtain carbon dots solid powder with an average size of 9 nm.

The 300 mg of carbon dots (i.e., the obtained carbon dots solid powder) and 20 mg of palladium chloride are added into a mixed solution of 10 mL of water and 40 mL of ethanol to obtain a system, and then the system is stirred for 6 h, followed by standing the system for 10 h. After standing the system for 10 h, 10 mL of $NaBH_4$ aqueous solution with a concentration of 2 $mg \cdot mL^{-1}$ is dropped into the above system to perform reduction for 1 h until the solution becomes a black suspension, and then the black suspension is centrifuged in a high-speed centrifuge for 20 min at a speed of 18000 rpm to obtain a solid emulsion catalyst.

The obtained solid emulsion catalyst is dispersed in water to prepare a dispersion A with a concentration of 3 wt %. The 10 mL of dispersion A and 5 mL of ethyl acetate are added into a vial to perform ultrasonic treatment for 1 min to obtain a mixture, and then the mixture is stirred for 20 min to emulsify the above mixture and form a Pickering miniemulsion, with a droplet size in a range of 0.1-1 μm. The 8 mmol of benzyl carbinol and 24 mmol of $H_2O_2$ are added into the catalytic system formed by the 10 mL of Pickering miniemulsion, and stirred evenly in an oil bath pot at 80° C. and reacted for 5 h. After the reaction, several drops of 1 M of hydrochloric acid solution are added into the system until demulsification, thus realizing oil-water stratification. Hyacinthin as a product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. The hyacinthin in the organic phase can be detected by gas chromatography with a yield of 99.9%. The water phase containing the catalyst can be used as the dispersion A to repeat the reaction step for recycling.

Embodiment 5

The 1.5 g of citric acid and 2 g of tetradecylamine are added into 25 mL of absolute ethanol to obtain a mixture, and the mixture is stirred for 3 h until the mixture is uniform. A precipitate of the mixture is filtered and washed several times with ethanol to obtain solid powder. The obtained solid powder is dried at 85° C. to obtain the dried powder (i.e., white powder), and then the dried powder is heated at 200° C. in air atmosphere for 1.5 h until the white powder is completely liquefied into orange liquid. Then, the 1 mL of orange liquid obtained above is dispersed dropwise into 20 mL of NaOH aqueous solution, and a concentration of NaOH is 0.25 M. And the NaOH aqueous solution added with the orange liquid is stirred at 35° C. for 36 h to obtain a dispersion. Finally, the obtained dispersion is centrifuged in a high-speed centrifuge for 8 min at a rotation speed of 8000 rpm to obtain a centrifuged supernatant. The centrifuged supernatant is treated with a 500 DA dialysis membrane for 36 h to remove small molecular impurities and obtain yellow carbon dots solution. The obtained yellow carbon dots solution is placed in an environment of −20° C. until it is completely frozen and then dried in a freeze dryer for 4 days to obtain carbon dots solid powder with an average size of 12 nm.

The 600 mg of carbon dots (i.e., the obtained carbon dots solid powder) and 30 mg of palladium chloride are added into a mixed solution of 10 mL of water and 40 mL of ethanol to obtain a system, and then the system is stirred for 6 h, followed by standing the system for 10 h. After standing the system for 10 h, 10 mL of $NaBH_4$ aqueous solution with a concentration of 2 $mg \cdot mL^{-1}$ is dropped into the above system to perform reduction for 1 h until the solution becomes a black suspension, and then the black suspension is centrifuged in a high-speed centrifuge for 20 min at a speed of 18000 rpm to obtain a solid emulsion catalyst.

The obtained solid emulsion catalyst is dispersed in water to prepare a dispersion A with a concentration of 3 wt %. The 10 mL of dispersion A and 5 mL of decahydronaphthalene are added into a vial to perform ultrasonic treatment for 2 min to obtain a mixture, and then the mixture is stirred for 20 min to emulsify the above mixture and form a Pickering miniemulsion, with a droplet size in a range of 0.1-1 μm. The 10 mmol of styrene and 30 mmol of $NaBH_4$ are added into the catalytic system formed by the 10 mL of Pickering miniemulsion, and stirred evenly in an oil bath pot at 40° C. and reacted for 0.5 h. After the reaction, several drops of 1 M of sulfuric acid solution are added into the system until demulsification, thus realizing oil-water stratification. Ethylbenzene as a product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. The ethylbenzene in the organic phase can be detected by gas chromatography with a yield of 100%. The water phase containing the catalyst can be used as the dispersion A to repeat the reaction step for recycling, and the catalyst activity is not attenuated after 3 times of recycling reaction.

Embodiment 6

The 1 g of citric acid and 4 g of octadecylamine are added into 25 mL of absolute ethanol to obtain a mixture, and the mixture is stirred for 2 h until the mixture is uniform. A precipitate of the mixture is filtered and washed several times with ethanol to obtain solid powder. The obtained solid powder is dried at 80° C. to obtain the dried powder (i.e., white powder), and then the dried powder is heated at 200° C. in air atmosphere for 1.5 h until the white powder is completely liquefied into orange liquid. Then, the 3 mL of orange liquid obtained above is dispersed dropwise into 60 mL of NaOH aqueous solution, and a concentration of NaOH is 0.25 M. And the NaOH aqueous solution added with the orange liquid is stirred at 45° C. for 36 h to obtain a dispersion. Finally, the obtained dispersion is centrifuged in a high-speed centrifuge for 8 min at a rotation speed of 9000 rpm to obtain a centrifuged supernatant. The centrifuged supernatant is treated with a 500 DA dialysis membrane for 48 h to remove small molecular impurities and obtain yellow carbon dots solution. The obtained yellow carbon dots solution is placed in an environment of −20° C. until it is completely frozen and then dried in a freeze dryer for 5 days to obtain carbon dots solid powder with an average size of 11 nm.

The 300 mg of carbon dots (i.e., the obtained carbon dots solid powder) and 20 mg of ruthenium chloride are added into a mixed solution of 10 mL of water and 40 mL of ethanol to obtain a system, and then the system is stirred for 6 h, followed by standing the system for 10 h. After standing the system for 10 h, 10 mL of NaBH$_4$ aqueous solution with a concentration of 2 mg·mL$^{-1}$ is dropped into the above system to perform reduction for 1 h until the solution becomes a black suspension, and then the black suspension is centrifuged in a high-speed centrifuge for 20 min at a speed of 18000 rpm to obtain a solid emulsion catalyst.

The obtained solid emulsion catalyst is dispersed in water to prepare a dispersion A with a concentration of 5 wt %. The 10 mL of dispersion A and 5 mL of toluene are added into a vial to perform ultrasonic treatment for 1 min to obtain a mixture, and then the mixture is stirred for 20 min to emulsify the above mixture and form a Pickering miniemulsion, with a droplet size in a range of 0.1-1 μm. The 8 mmol of furfuryl alcohol and 24 mmol of H$_2$O$_2$ are added into the catalytic system formed by the 10 mL of Pickering miniemulsion, and stirred evenly in an oil bath pot at 80° C. and reacted for 3 h. After the reaction, several drops of 1 M of hydrochloric acid solution are added into the system until demulsification, thus realizing oil-water stratification. Furfural as a product of the reaction is dissolved in an organic phase and a catalyst of the reaction is dispersed in a water phase. After adding several drops of NaOH solution (1 M) to tune the pH value to 10-11, the Pickering miniemulsion is regenerated by stirring. The furfural in the organic phase can be detected by gas chromatography with a yield of 89%. The water phase containing the catalyst can be used as the dispersion A to repeat the reaction step for recycling, and the catalyst activity is not attenuated after 2 times of recycling reaction.

Embodiment 7

The 2 g of citric acid and 2 g of tetradecylamine are added into 25 mL of absolute ethanol to obtain a mixture, and the mixture is stirred for 1 h until the mixture is uniform. A precipitate of the mixture is filtered and washed several times with ethanol to obtain solid powder. The obtained solid powder is dried at 40° C. for 24 h to obtain the dried powder (i.e., white powder), and then the dried powder is heated at 200° C. in air atmosphere for 1.5 h until the white powder is completely liquefied into orange liquid. Then, the 5 mL of orange liquid obtained above is dispersed dropwise into 100 mL of NaOH aqueous solution, and a concentration of NaOH is 0.25 M. And the NaOH aqueous solution added with the orange liquid is stirred at 35° C. for 48 h to obtain a dispersion. Finally, the obtained dispersion is centrifuged in a high-speed centrifuge for 10 min at a rotation speed of 9000 rpm to obtain a centrifuged supernatant. The centrifuged supernatant is treated with a 500 DA dialysis membrane for 48 h to remove small molecular impurities and obtain yellow carbon dots solution. The obtained yellow carbon dots solution is placed in an environment of −30° C. for 6 h until it is completely frozen and then dried in a freeze dryer for 5 days to obtain carbon dots solid powder with an average size of 10 nm.

The 100 mg of carbon dots (i.e., the obtained carbon dots solid powder) and 20 mg of palladium chloride are added into a mixed solution of 10 mL of water and 40 mL of ethanol to obtain a system, and then the system is stirred for 4 h, followed by standing the system for 12 h. After standing the system for 12 h, 10 mL of NaBH$_4$ aqueous solution with a concentration of 2 mg·mL$^{-1}$ is dropped into the above system to perform reduction for 1 h until the solution became a black suspension, and then the black suspension is centrifuged in a high-speed centrifuge for 20 min at a speed of 20000 rpm to obtain a solid emulsion catalyst.

The obtained solid emulsion catalyst is dispersed in water to prepare a dispersion A with a concentration of 1 wt %. The 4 mL of dispersion A and 2 mL of toluene are added into a vial to perform ultrasonic treatment for 0.5 min to obtain a mixture, and then the mixture is stirred for 10 min to emulsify the above mixture and form a Pickering miniemulsion, with a droplet size in a range of 0.1-1 μm. The 2 mmol of cinnamyl alcohol and 6 mmol of H$_2$O$_2$ are added into the catalytic system formed by the 6 mL of Pickering miniemulsion, and stirred evenly in an oil bath pot at 80° C. and reacted for 60 h. After the reaction, several drops of 1 M of hydrochloric acid solution are added into the system until demulsification, thus realizing oil-water stratification. After adding several drops of NaOH solution (1 M) to tune the pH value to 10-11, the Pickering miniemulsion is regenerated by stirring. Cinnamaldehyde as a product in the toluene is detected by gas chromatography with a yield of 98%, and a water phase containing the catalyst can be used as the dispersion A to repeat the reaction step for recycling, and the catalyst activity is not attenuated after 3 times of recycling reaction.

Embodiment 8

The 2 g of citric acid and 0.5 g of octadecylamine are added into 25 mL of absolute ethanol to obtain a mixture, and the mixture is stirred for 1 h until the mixture is uniform. A precipitate of the mixture is filtered and washed several times with ethanol to obtain solid powder. The obtained solid powder is dried at 50° C. for 24 h to obtain the dried powder (i.e., white powder), and then the dried powder is heated at 200° C. in air atmosphere for 2 h until the white powder is completely liquefied into orange liquid. Then, the orange liquid obtained above is dispersed dropwise into 100 mL of NaOH aqueous solution, and a concentration of NaOH is 0.25 M. And the NaOH aqueous solution added with the orange liquid is stirred at 40° C. for 48 h to obtain a dispersion. Finally, the obtained dispersion is centrifuged in a high-speed centrifuge for 10 min at a rotation speed of 9000 rpm to obtain a centrifuged supernatant. The centrifuged supernatant is treated with a 500 DA dialysis membrane for 48 h to remove small molecular impurities and obtain yellow carbon dots solution. The obtained yellow carbon dots solution is placed in an environment of −30° C. for 6 h until it is completely frozen and then dried in a freeze dryer for 5 days to obtain carbon dots solid powder with an average size of 11 nm.

The 200 mg of carbon dots (i.e., the obtained carbon dots solid powder) and 20 mg of ruthenium chloride are added into 25 mL of a mixed solution of water and ethanol (a volume ratio of water to ethanol is 1:4) to obtain a system, and then the system is stirred for 4 h, followed by standing the system for 12 h. After standing the system for 12 h, 10 mL of $NaBH_4$ aqueous solution with a concentration of 2 $mg \cdot mL^{-1}$ is dropped into the above system to perform reduction for 1 h until the solution becomes a black suspension, and then the black suspension is centrifuged in a high-speed centrifuge for 20 min at a speed of 20000 rpm to obtain a solid emulsion catalyst.

The obtained solid emulsion catalyst is dispersed in water to prepare a dispersion A with a concentration of 3 wt %. The 4 mL of dispersion A and 2 mL of cyclohexane are added into a vial to perform ultrasonic treatment for 0.5 min to obtain a mixture, and then the mixture is stirred for 10 min to emulsify the above mixture and form a Pickering miniemulsion, with a droplet size in a range of 0.1-1 μm. The 2 mmol of P-chloronitrobenzene and 6 mmol of $NaBH_4$ are added into the catalytic system formed by the 6 mL of Pickering miniemulsion, and stirred evenly in an oil bath pot at 50° C. and reacted for 2 h. After the reaction, several drops of 1 M of sulfuric acid solution are added into the system until demulsification, thus realizing oil-water stratification. After adding several drops of NaOH solution (1 M) to tune the pH value to 10-11, the Pickering miniemulsion is regenerated by stirring. P-chloroaniline as a product in the cyclohexane is detected by gas chromatography with a yield of 88%. A water phase containing the catalyst can be used as the dispersion A to repeat the reaction step for recycling, and the catalyst activity is not attenuated after 5 times of recycling reaction.

It should be understood that the above-mentioned embodiments only illustrate the technical concept and characteristics of the disclosure, and their purpose is to enable people familiar with this technology to understand the content of the disclosure and implement it accordingly, and not to limit the scope of protection of the disclosure. All equivalent changes or modifications made according to the spirit of the disclosure should be included in the protection scope of the disclosure. Although the specific embodiments of the disclosure have been described with the attached drawings, they are not limitations on the scope of protection of the disclosure. Those skilled in the art should understand that on the basis of the technical scheme of the disclosure, various modifications or deformations that can be made by those skilled in the art without creative labor are still within the scope of protection of the disclosure.

What is claimed is:

1. A method for constructing a Pickering miniemulsion catalytic system, comprising the following steps:
   step 1, preparing a Pickering miniemulsion catalyst/emulsifier, specifically comprising:
      step 1.1, preparation of surface-modified carbon quantum dots:
         adding citric acid and an amine compound to absolute ethanol, and modifying carbon dots by using the amine compound as a modifier and the citric acid as a carbon source, and heating for obtaining orange liquid; wherein 1.5-3 g of the citric acid and 0.1-4 g of the amine compound are added into every 25 mL of the absolute ethanol;
         dispersing the orange liquid into sodium hydroxide (NaOH) aqueous solution dropwise, and stirring the NaOH aqueous solution added with the orange liquid at 35-50° C. for 24-48 h to obtain a dispersion; wherein a volume ratio of the NaOH aqueous solution to the orange liquid is 20:1; and
         centrifuging the dispersion to obtain a supernatant, treating the supernatant with 500 Dalton (DA) dialysis membrane for 24-48 h to remove small molecular impurities and obtain yellow carbon dots solution; placing the yellow carbon dots solution in an environment below −10° C. until the yellow carbon dots solution is completely frozen, and then drying in a freeze dryer to obtain carbon dots solid powder with a size of 8-12 nm;
      step 1.2, preparation of an emulsion catalyst:
         adding the carbon dots solid powder and a metal salt into a mixed solution of water and ethanol and then stirring for 3-6 h to obtain a system; wherein 20-1000 mg of the carbon dots solid powder and 1-50 mg of the metal salt are correspondingly added into every 50 mL of the mixed solution of water and ethanol, and a volume ratio of the water to the ethanol in the mixed solution of water and ethanol is 1:4; after standing the system for 6-18 h, adding sodium borohydride ($NaBH_4$) aqueous solution dropwise into the system to perform reduction for 0.5-2 h until the system becomes a black suspension, and centrifuging the black suspension to obtain a solid emulsion catalyst; wherein 10 mL of the $NaBH_4$ aqueous solution with a concentration of 2 $mg \cdot mL^{-1}$ is correspondingly added to every 50 mL of the mixed solution of water and ethanol;
   step 2, constructing the Pickering miniemulsion catalytic system, specifically comprising:
      dispersing the obtained solid emulsion catalyst in water to prepare a dispersion A with a concentration of 0.05-5 wt %; adding the dispersion A to a vial with a water-immiscible organic solvent to obtain a mixture; wherein a volume ratio of the dispersion A to the organic solvent is 2:1; performing ultrasonic treatment on the mixture in the vial for 0.5-2 min, and then stirring the mixture for 10-20 min to emulsify the mixture and form a Pickering miniemulsion; and wherein a droplet size of the Pickering miniemulsion is in a range of 0.1-1 μm.

2. The method for constructing the Pickering miniemulsion catalytic system as claimed in claim 1, wherein in step 1.1, the amine compound is one selected from the group consisting of dodecylamine, tetradecylamine, hexadecylamine, and octadecylamine.

3. The method for constructing the Pickering miniemulsion catalytic system as claimed in claim 1, wherein in step 1.1, a centrifuging speed is in a range of 6000 rpm to 9000 rpm, and a centrifuging time is in a range of 5 min to 10 min; and
   wherein in step 1.2, a centrifuging speed is in a range of 18000 rpm to 26000 rpm, and a centrifuging time is in a range of 15 min to 35 min.

4. The method for constructing the Pickering miniemulsion catalytic system as claimed in claim 1, wherein in step 1.2, the metal salt is one selected from the group consisting of ruthenium chloride, palladium chloride and chloroplatinic acid.

5. The method for constructing the Pickering miniemulsion catalytic system as claimed in claim 1, wherein in step 2, the organic solvent is one selected from the group consisting of toluene, cyclohexane, dichloromethane, ethyl acetate, and decalin.

6. An application method of the Pickering miniemulsion catalytic system constructed by the method as claimed in claim 1, comprising:

applying the Pickering miniemulsion catalytic system in a biphasic catalytic reaction.

7. The application method as claimed in claim 6, wherein the applying the Pickering miniemulsion catalytic system in a biphasic catalytic reaction, comprises:

adding a reactant and a water-soluble oxidant/reductant into the Pickering miniemulsion catalytic system, then uniformly stirring in an oil bath pot at 30-90° C. and reacting for 0.5-5 h; wherein a molar ratio of the reactant to the water-soluble oxidant/reductant is 1:3, and 2-10 mmol of the reactant are added into every 10 mL of the Pickering miniemulsion catalytic system; after the reacting, adding 1 M of inorganic acid solution dropwise into the Pickering miniemulsion catalytic system until demulsification and realizing oil-water stratification; wherein a product of the reacting is dissolved in an organic phase and a catalyst of the reacting is dispersed in a water phase, the product in the organic phase is detected by gas chromatography to obtain a yield, the water phase containing the catalyst is used as the dispersion A for repeated use in step 2; after adding several drops of NaOH solution (1 M) to tune a pH value to 10-11, the Pickering miniemulsion is regenerated by stirring; and the inorganic acid solution is one selected from the group consisting of hydrochloric acid, sulfuric acid, and nitric acid.

8. The application method as claimed in claim 7, wherein the reactant comprises alcohol, olefin or a nitro compound; the water-soluble oxidant is hydrogen peroxide ($H_2O_2$), and the reductant is $NaBH_4$.

* * * * *